United States Patent
McCabe et al.

(10) Patent No.: US 8,639,317 B2
(45) Date of Patent: *Jan. 28, 2014

(54) WIRELESS ECG IN IMPLANTABLE DEVICES

(71) Applicant: Cardiac Pacemakers, Inc., St. Paul, MN (US)

(72) Inventors: Aaron R. McCabe, Edina, MN (US); Avram Scheiner, Vadnais Heights, MN (US); Geng Zhang, Newbury Park, CA (US); Douglas R. Daum, Woodbury, MN (US); Yi Zhang, Plymouth, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/657,224

(22) Filed: Oct. 22, 2012

(65) Prior Publication Data

US 2013/0046195 A1    Feb. 21, 2013

Related U.S. Application Data

(60) Continuation of application No. 13/288,105, filed on Nov. 3, 2011, now Pat. No. 8,301,234, which is a division of application No. 12/893,127, filed on Sep. 29, 2010, now Pat. No. 8,055,332, which is a division of application No. 11/925,657, filed on Oct. 26, 2007, now Pat. No. 7,818,051, which is a division of application No. 10/795,126, filed on Mar. 5, 2004, now Pat. No. 7,299,086.

(51) Int. Cl.
*A61B 5/04* (2006.01)

(52) U.S. Cl.
USPC ........................................................ 600/515

(58) Field of Classification Search
USPC .............. 607/2, 4–5, 9, 25–26; 600/508–510, 600/515
See application file for complete search history.

(56) References Cited

U.S. PATENT DOCUMENTS

| 4,333,470 A | 6/1982 | Barthel |
| 4,539,999 A | 9/1985 | Mans |

(Continued)

FOREIGN PATENT DOCUMENTS

| EP | 0308536 A1 | 3/1989 |
| EP | 744190 A2 | 11/1996 |

(Continued)

OTHER PUBLICATIONS

"U.S. Appl. No. 10/795,126, Examiner Interview Summary filed Oct. 9, 2007", 1 pg.

(Continued)

*Primary Examiner* — Eric D. Bertram
*Assistant Examiner* — Elizabeth K So
(74) *Attorney, Agent, or Firm* — Schwegman Lundberg & Woessner, P.A.

(57) ABSTRACT

An implantable medical device such as an implantable pacemaker or implantable cardioverter/defibrillator includes a programmable sensing circuit providing for sensing of a signal approximating a surface electrocardiogram (ECG) through implanted electrodes. With various electrode configurations, signals approximating various standard surface ECG signals are acquired without the need for attaching electrodes with cables onto the skin. The various electrode configurations include, but are not limited to, various combinations of intracardiac pacing electrodes, portions of the implantable medical device contacting tissue, and electrodes incorporated onto the surface of the implantable medical device.

20 Claims, 11 Drawing Sheets

(56) References Cited

U.S. PATENT DOCUMENTS

| | | | |
|---|---|---|---|
| 4,585,004 | A | 4/1986 | Brownlee |
| RE32,378 | E | 3/1987 | Barthel |
| 4,662,382 | A | 5/1987 | Sluetz et al. |
| 5,040,533 | A | 8/1991 | Fearnot |
| 5,113,869 | A | 5/1992 | Nappholz et al. |
| 5,127,401 | A | 7/1992 | Grevious et al. |
| 5,265,602 | A | 11/1993 | Anderson et al. |
| 5,324,310 | A | 6/1994 | Greeninger et al. |
| 5,331,966 | A | 7/1994 | Bennett et al. |
| 5,360,437 | A | 11/1994 | Thompson |
| 5,366,487 | A | 11/1994 | Adams et al. |
| 5,378,775 | A | 1/1995 | Shimizu et al. |
| 5,379,775 | A | 1/1995 | Kruse |
| 5,439,481 | A | 8/1995 | Adams |
| 5,448,997 | A | 9/1995 | Kruse et al. |
| 5,456,692 | A | 10/1995 | Smith, Jr. et al. |
| 5,503,160 | A | 4/1996 | Pering et al. |
| 5,531,767 | A | 7/1996 | Fain |
| 5,630,425 | A | 5/1997 | Panescu |
| 5,725,559 | A | 3/1998 | Alt et al. |
| 5,776,168 | A | 7/1998 | Gunderson |
| 5,843,138 | A | 12/1998 | Evers et al. |
| 5,935,081 | A | 8/1999 | Kadhiresan |
| 5,954,662 | A | 9/1999 | Swanson et al. |
| 6,073,049 | A | 6/2000 | Alt et al. |
| 6,088,618 | A | 7/2000 | Kerver |
| 6,134,463 | A | 10/2000 | Wittkampf et al. |
| 6,157,859 | A | 12/2000 | Alt |
| 6,161,042 | A | 12/2000 | Hartley et al. |
| 6,169,918 | B1 | 1/2001 | Haefner et al. |
| 6,179,865 | B1 | 1/2001 | Hsu et al. |
| 6,201,993 | B1 | 3/2001 | Kruse et al. |
| 6,230,059 | B1 | 5/2001 | Duffin |
| 6,334,071 | B1 | 12/2001 | Lu |
| 6,405,083 | B1 | 6/2002 | Rockwell et al. |
| 6,418,340 | B1 | 7/2002 | Conley et al. |
| 6,456,871 | B1 | 9/2002 | Hsu et al. |
| 6,477,404 | B1 | 11/2002 | Yonce et al. |
| 6,480,733 | B1 | 11/2002 | Turcott |
| 6,493,579 | B1 | 12/2002 | Gilkerson et al. |
| 6,496,715 | B1 | 12/2002 | Lee et al. |
| 6,505,067 | B1 | 1/2003 | Lee et al. |
| 6,512,940 | B1 | 1/2003 | Brabec et al. |
| 6,522,917 | B1 | 2/2003 | Hsu et al. |
| 6,522,925 | B1 | 2/2003 | Gilkerson et al. |
| 6,526,313 | B2 | 2/2003 | Sweeney et al. |
| 6,589,187 | B1 | 7/2003 | Dirnberger et al. |
| 6,636,963 | B1 | 10/2003 | Stein et al. |
| 6,658,283 | B1 | 12/2003 | Bornzin et al. |
| 6,687,540 | B2 | 2/2004 | Marcovecchio |
| 6,745,068 | B2 | 6/2004 | Koyrakh et al. |
| 6,889,079 | B2 | 5/2005 | Bocek et al. |
| 6,925,326 | B1 | 8/2005 | Levine et al. |
| 7,212,849 | B2 | 5/2007 | Zhang et al. |
| 7,228,176 | B2 | 6/2007 | Smith et al. |
| 7,277,754 | B2 | 10/2007 | McCabe et al. |
| 7,299,086 | B2 | 11/2007 | McCabe et al. |
| 7,567,836 | B2 | 7/2009 | Zhang |
| 7,684,861 | B2 | 3/2010 | Sanders |
| 7,751,890 | B2 | 7/2010 | McCabe et al. |
| 7,818,051 | B2 | 10/2010 | McCabe et al. |
| 8,301,234 | B2 | 10/2012 | McCabe et al. |
| 2002/0049474 | A1 | 4/2002 | Marcovecchio et al. |
| 2002/0065539 | A1 | 5/2002 | Von Arx et al. |
| 2002/0072778 | A1 | 6/2002 | Guck et al. |
| 2002/0107552 | A1 | 8/2002 | Krig et al. |
| 2002/0123768 | A1 | 9/2002 | Gilkerson |
| 2002/0123769 | A1 | 9/2002 | Panken et al. |
| 2002/0143372 | A1 | 10/2002 | Snell et al. |
| 2002/0161410 | A1 | 10/2002 | Kramer et al. |
| 2002/0198461 | A1 | 12/2002 | Hsu et al. |
| 2003/0004552 | A1 | 1/2003 | Plombon et al. |
| 2003/0040676 | A1 | 2/2003 | Prentice et al. |
| 2003/0050563 | A1 | 3/2003 | Suribhotla et al. |
| 2003/0060849 | A1 | 3/2003 | Hsu |
| 2003/0069609 | A1 | 4/2003 | Thompson |
| 2003/0083586 | A1 | 5/2003 | Ferek-Petric |
| 2003/0105491 | A1 | 6/2003 | Gilkerson et al. |
| 2003/0109792 | A1 | 6/2003 | Hsu et al. |
| 2003/0114889 | A1 | 6/2003 | Huvelle et al. |
| 2003/0120316 | A1 | 6/2003 | Spinelli et al. |
| 2003/0208238 | A1 | 11/2003 | Weinberg et al. |
| 2004/0015090 | A1 | 1/2004 | Sweeney et al. |
| 2004/0093035 | A1 | 5/2004 | Schwartz et al. |
| 2004/0116820 | A1 | 6/2004 | Daum et al. |
| 2004/0116972 | A1 | 6/2004 | Marcovecchio |
| 2004/0127950 | A1 | 7/2004 | Kim et al. |
| 2004/0215240 | A1 | 10/2004 | Lovett et al. |
| 2004/0230229 | A1 | 11/2004 | Lovett et al. |
| 2005/0010257 | A1 | 1/2005 | Lincoln et al. |
| 2005/0107839 | A1 | 5/2005 | Sanders |
| 2005/0149134 | A1 | 7/2005 | McCabe et al. |
| 2005/0159781 | A1 | 7/2005 | Hsu |
| 2006/0015148 | A1 | 1/2006 | McCabe et al. |
| 2006/0095083 | A1 | 5/2006 | Zhang et al. |
| 2007/0167849 | A1 | 7/2007 | Zhang et al. |
| 2007/0179392 | A1 | 8/2007 | Zhang |
| 2007/0299356 | A1 | 12/2007 | Wariar et al. |
| 2010/0145406 | A1 | 6/2010 | Sanders |
| 2012/0053474 | A1 | 3/2012 | Mccabe et al. |

FOREIGN PATENT DOCUMENTS

| | | |
|---|---|---|
| EP | 0784996 A1 | 7/1997 |
| WO | WO-9401173 A1 | 1/1994 |
| WO | WO-2005089643 A1 | 9/2005 |
| WO | WO-2006049767 A1 | 5/2006 |

OTHER PUBLICATIONS

"U.S. Appl. No. 10/795,126, Non-Final Office Action mailed Jan. 25, 2007", 11 pgs.

"U.S. Appl. No. 10/795,126, Notice of Allowance mailed Jul. 9, 2007", 10 pgs.

"U.S. Appl. No. 10/795,126, Response filed Apr. 25, 2007 to Non Final Office Action mailed Jan. 25, 2007", 11 pgs.

"U.S. Appl. No. 10/795,126, Response filed Nov. 6, 2006 to Restriction Requirement mailed Oct. 6, 2006", 18 pgs.

"U.S. Appl. No. 10/795,126, Restriction Requirement mailed Oct. 6, 2006", 10 pgs.

"U.S. Appl. No. 10/795,126, Supplemental Notice of Allowability mailed Oct. 10, 2007", 3 pgs.

"U.S. Appl. No. 11/693,110, Non-Final Office Action mailed Apr. 28, 2011", 11 pgs.

"U.S. Appl. No. 11/925,657, Final Office Action mailed Mar. 9, 2010", 9 pgs.

"U.S. Appl. No. 11/925,657, Non-Final Office Action mailed Aug. 21, 2009", 8 pgs.

"U.S. Appl. No. 11/925,657, Notice of Allowance mailed Jun. 24, 2010", 6 pgs.

"U.S. Appl. No. 11/925,657, Response filed May 10, 2010 to Final Office Action mailed Mar. 9, 2010", 7 pgs.

"U.S. Appl. No. 11/925,657, Response filed Nov. 23, 2009 to Non Final Office Action mailed Aug. 21, 2009", 11 pgs.

"U.S. Appl. No. 12/893,127, Non Final Office Action mailed Mar. 28, 2011", 9 pgs.

"U.S. Appl. No. 12/893,127, Notice of Allowance mailed Sep. 12, 2011", 5 pgs.

"U.S. Appl. No. 12/893,127, Response filed Jun. 28, 2011 to Non Final Office Action mailed Mar. 28, 2011", 15 pgs.

"U.S. Appl. No. 13/288,105, Response to Rule 312 mailed Oct. 1, 2012", 2 pgs.

"U.S. Appl. No. 13/288,105, Notice of Allowance mailed Jun. 18, 2012", 12 pgs.

"International Application Serial No. PCT/US2005/006984, International Search Report mailed Aug. 4, 2005", 13 pgs.

"New Diagnostic Tool—Reveal Insertable Loop Recorder", http://www.medtronic.com/reveal/new.html, (Archived Sep. 19, 2000), 3 Pages.

(56) References Cited

OTHER PUBLICATIONS

Hsu, William, "System and Method for Classifying Tachycardia Arrhythmias Having 1:1 Atrial to Ventricular Rhythms", U.S. Appl. No. 09/417,588, filed Oct. 13, 1999, 39 pgs.

Hughes, Howard C, et al., "The Effects of Electrode Position on the Detection of the Transvenous Cardiac Electrogram", PACE, vol. 3, (Nov.-Dec. 1980), 651-655.

Leitch, James, et al., "Feasibility of an implantable arrhythmia monitor", PACE, vol. 15, No. 12, (Dec. 1992), 2232-5.

Mazur, Alexander, "Functional similarity between electrograms recorded from an implantable cardioverter defibrillator emulator and the surface electrocardiogram", PACE, vol. 24, (Jan. 2001), 34-40.

Theres, Heinz, et al., "Electrogram signals recorded from acute and chronic pacemaker implantation sites in pacemaker patie", PACE, vol. 21, Part 1, (Jan. 1998), 11-17.

WIRELESS ECG IN IMPLANTABLE DEVICES

CLAIM OF PRIORITY

This application is a continuation of and claims the benefit of priority under 35 U.S.C. §120 to U.S. patent application Ser. No. 13/288,105, filed on Nov. 3, 2011, now issued as U.S. Pat. No. 8,301,234, which is a divisional of and claims the benefit of priority under 35 U.S.C. §120 to U.S. patent application Ser. No. 12/893,127, filed on Sep. 29, 2010, now issued as U.S. Pat. No. 8,055,332, which is a divisional of and claims the benefit of priority under 35 U.S.C. §120 to U.S. patent application Ser. No. 11/925,657, filed on Oct. 26, 2007, now issued as U.S. Pat. No. 7,818,051, which is a divisional of and claims the benefit of priority under 35 U.S.C. §120 to U.S. patent application Ser. No. 10/795,126, filed on Mar. 5, 2004, now issued as U.S. Pat. No. 7,299,086, which are hereby incorporated by reference in their entirety.

CROSS-REFERENCE TO RELATED APPLICATION

This application is related to commonly assigned U.S. patent application Ser. No. 10/712,776, entitled "IMPLANTABLE CARDIAC MONITOR UPGRADEABLE TO PACEMAKER OR CARDIAC RESYNCHRONIZATION DEVICE," filed on Nov. 13, 2003, now issued as U.S. Pat. No. 7,684,861, and U.S. patent application Ser. No. 10/746,855, entitled "WIRELESS ECG PACE AVOIDANCE AND DISPLAY METHOD," filed on Dec. 24, 2003, now issued as U.S. Pat. No. 7,277,754, which are hereby incorporated by reference in their entirety.

FIELD OF THE INVENTION

This document generally relates to cardiac rhythm management (CRM) systems and particularly, but not by way of limitation, to such systems using an implantable medical device to sense a signal that approximates a surface electrocardiogram (ECG).

BACKGROUND

The heart is the center of a person's circulatory system. It includes a complex electro-mechanical system that draws oxygenated blood from the lungs and pumps it to the organs of the body to provide the organs with their metabolic needs for oxygen, and draws deoxygenated blood from the organs and pumps it into the lungs where the blood gets oxygenated. In a heart having a normal electrical system, the sinoatrial node, the heart's natural pacemaker, generates electrical signals, called action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently. The function of the electrical system is indicated by a biopotential signal sensed with at least two electrodes attached on the skin or implanted in the body. When the electrical system functions abnormally, the biopotential signal shows that contractions at one or more cardiac regions are chaotic and asynchronized. Such conditions are known as cardiac arrhythmias. Timing and morphological information contained in the biopotential signal is used to diagnose the type of arrhythmia and/or determine an appropriate therapy.

When the biopotential signal is sensed with electrodes attached onto the skin, the sensed signal is commonly referred to as surface electrocardiogram (ECG), or simply ECG. Various standard ECG signals (vectors) are recorded for diagnostic purposes with different combinations of electrode locations. When the electrodes are implanted underneath the skin, the sensed signal is referred to as subcutaneous ECG or far-field electrogram. When at least one electrode is placed in or on the heart, the sensed signal is referred to as electrogram or intracardiac electrogram. Surface ECG is widely used for diagnostic purposes and provides for information on the global electrical performance of the heart. Subcutaneous ECG is known to closely approximate the surface ECG. In contrast, intracardiac electrogram indicates localized electrical performance and may not contain sufficient information for general diagnostic purposes. Implantable medical devices such as cardiac pacemakers and cardioverter/defibrillators sense intracardiac electrograms for timing the delivery of therapeutic electrical energy. Though such an implantable medical device is capable of acquiring intracardiac electrograms and transmitting the electrograms for display in an external device, physicians may still need the surface ECG for diagnostic and therapeutic purposes. The skin contact electrodes and the cables connecting the electrodes to an ECG recorder, as required for recording the surface ECG, may become cumbersome, for example, during an operation such as the implantation of the implantable medical device or during a patient examination where ECG is recorded during exercise. Regular in-home ECG monitoring may be impractical in the absence of a physician or other trained caregiver.

While studies have shown that signals acquired with implanted electrodes of certain configurations approximate surface ECG signals, there is a need to implement a system to acquire a signal substituting for various standard surface ECG signals using an implantable medical device.

SUMMARY

A CRM system includes an implantable medical device such as an implantable pacemaker or implantable cardioverter/defibrillator. The implantable medical device includes a programmable sensing circuit providing for sensing of a signal approximating a surface ECG through implanted electrodes. With various electrode configurations, signals approximating various standard surface ECG signals are acquired without the need for attaching electrodes with cables onto the skin.

In one embodiment, a CRM system includes a plurality of implantable electrodes and an implantable device. The implantable electrodes include at least a first electrode and a second electrode selectable for sensing a cardiac signal approximating a surface ECG. The implantable medical device includes a sensing circuit, a processor, and a programmable sense interface. The sensing circuit includes a first sense input and a second sense input being a pair of differential inputs for sensing the cardiac signal approximating the surface ECG. The gain of the sensing circuit is programmable for at least a surface ECG gain selectable for sensing the cardiac signal approximating the surface ECG and an electrogram gain selectable for sensing an intracardiac electrogram. The frequency response of the sensing circuit is programmable for at least a surface ECG pass band selectable for sensing the cardiac signal approximating the surface ECG and an intracardiac electrogram pass band selectable for sensing an intracardiac electrogram. The processor controls the operation of the sensing circuit. It includes a command receiver to receive an ECG acquisition command. The programmable sense interface provides at least a first electrical connection and a second electrical connection in response to the ECG acquisition command. The first electrical connection connects the first electrode to the first sense input. The second electrical connection connects the second electrode to the second sense input.

In one embodiment, a CRM system includes a plurality of implantable electrodes and an implantable medical device. The plurality of implantable electrodes are incorporated onto the implantable medical device and configured for sensing cardiac signals each approximating a surface ECG vector. The implantable medical device includes a sensing circuit, a processor, and a programmable sense interface. The sensing circuit includes a plurality of sensing channels providing for simultaneous sensing of the cardiac signals. The processor controls the operation of the sensing circuit. It includes a command receiver to receive an ECG acquisition command. The programmable sense interface provides a plurality of pairs of electrical connections. Each pair connects between one of the plurality of sensing channels and two electrodes selected from the plurality of implantable electrodes.

In one embodiment, an implantable medical device includes a sensing circuit, a hermetically sealed can, and at least two concentric electrodes. The sensing circuit is programmable for a frequency response suitable for sensing a surface ECG, and includes a first sense input and a second sense input being a pair of differential inputs for sensing a cardiac signal. The hermetically sealed can houses a circuit including at least portions of the sensing circuit. The can has an outer surface subject to contact with body tissue. The concentric electrodes are incorporated onto the outer surface of the can. These concentric electrodes include at least an inner electrode and an outer electrode. The inner is coupled to the first sense input. The outer electrode is coupled to the second sense input.

In one embodiment, a method provides for acquisition of a signal approximating a surface ECG using an implantable medical device. The acquisition starts in response to receiving an ECG acquisition command. A pass band of a sensing circuit of the implantable medical device is programmed for a surface ECG pass band. A sense interface of the implantable medical device is programmed to electrically connect at least two electrodes to the sensing circuit. A cardiac signal is sensed after the sensing circuit and the sense interface are programmed.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document. The drawing are for illustrative purposes only and not to scale nor anatomically accurate.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses a cardiac rhythm management (CRM) system that provides for sensing of a signal approximating the surface ECG using an implantable medical device, thus eliminating the need of attaching skin contact electrodes and the wires/cables connecting the electrodes and an ECG recorder. Studies have shown signals sensed using electrodes implanted in certain locations within a body approximate the surface ECG, i.e., contain some or all of the information extractable from the surface ECG. Such signals are usable for diagnostic and other purposes as a substitute for the surface ECG.

In this document, a "user" includes a physician or other caregiver using the CRM system to treat a patient. "Surface ECG" includes a cardiac electrical signal sensed though electrodes attached to the skin surface. "Subcutaneous ECG"

includes a cardiac electrical signal sensed though implantable electrodes placed under the skin and is similar to the surface ECG in terms of characteristics and diagnostic information contained. "Electrogram" includes a cardiac electrical signal sensed though implantable electrodes placed in or on the heart. "Wireless ECG" includes a signal approximating the surface ECG, acquired without using surface (skin contact) electrodes.

Figure 1:
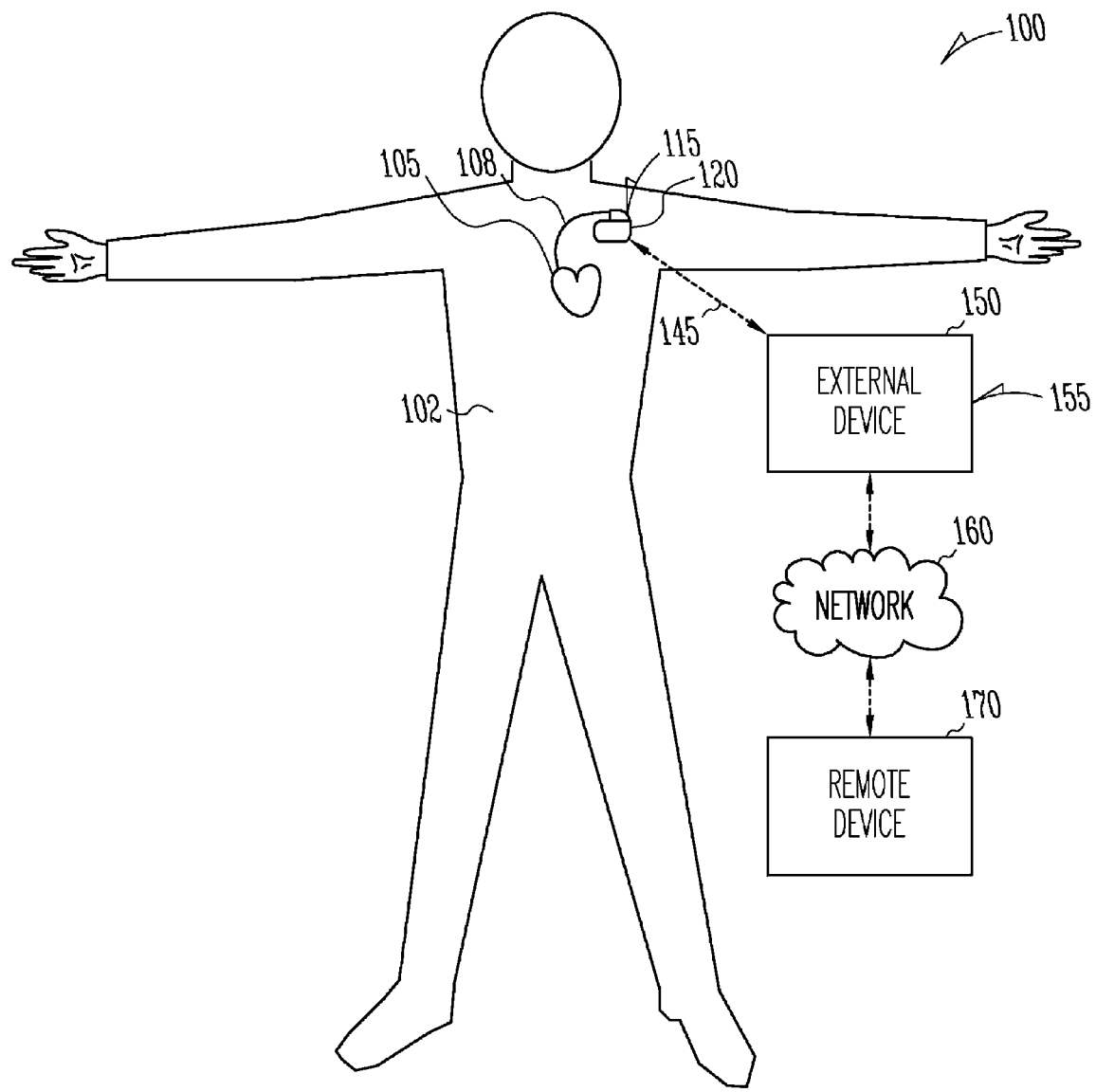
FIG. 1 is an illustration of an embodiment of a CRM system, including an implantable medical device and an external system, and portions of an environment in which it is used.

FIG. 1 is an illustration of an embodiment of portions of a CRM system 100 and portions of the environment in which system 100 is used. CRM system 100 includes an implantable system 115, an external system 155, and a telemetry link 145 providing for bidirectional communication between implantable system 115 and external system 155. Implantable system 115 includes an implantable medical device 120 and a lead system 108. Implantable medical device 120 is implanted within a body 102 and coupled to a heart 105 via lead system 108. Examples of implantable medical device 120 include, but are not limited to, pacemakers, pacemaker/defibrillators, cardiac resynchronization devices, cardiac remodeling control devices, and cardiac monitors. In one embodiment, lead system 108 includes multiple atrial and ventricular leads. In one embodiment, external system 155 includes a programmer. In another embodiment, external system 155 is a patient management system including an external device 150 in proximity of implantable device 140, a remote device 170 in a relatively distant location, and a telecommunication network 160 linking external device 150 and remote device 170. The patient management system allows access to implantable system 115 from a remote location, for purposes such as monitoring patient status and adjusting therapies. In one embodiment, telemetry link 145 is an inductive telemetry link. In an alternative embodiment, telemetry link 145 is a far-field radio-frequency telemetry link. In one embodiment, telemetry link 145 provides for data transmission from implantable medical device 120 to external system 155. This may include, for example, transmitting real-time physiological data acquired by implantable medical device 120, extracting physiological data acquired by and stored in implantable medical device 120, extracting therapy history data stored in implantable medical device 120, and extracting data indicating an operational status of implantable medical device 120 (e.g., battery status and lead impedance). In a further embodiment, telemetry link 145 provides for data transmission from external system 155 to implantable medical device 120. This may include, for example, programming implantable medical device 120 to acquire physiological data, programming implantable medical device 120 to perform at least one self-diagnostic test (such as for a device operational status), and programming implantable medical device 120 to deliver at least one therapy.

Figure 2A:
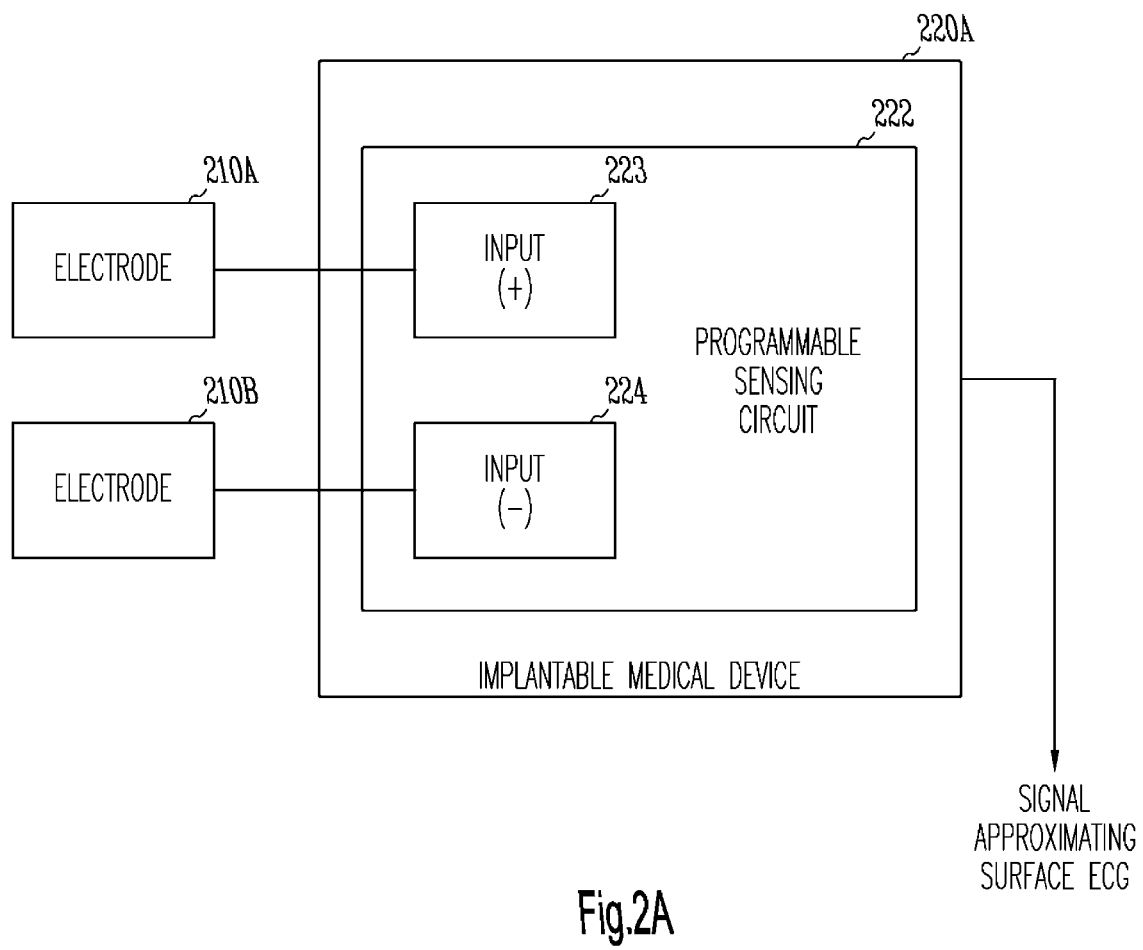
FIG. 2A is a block diagram illustrating one embodiment of portions of the circuit of the implantable medical device providing for wireless ECG sensing.

FIG. 2A is a block diagram illustrating one embodiment of portions of the circuit of an implantable medical device 220A providing for wireless ECG sensing. Implantable medical device 220A is a specific embodiment of implantable medical device 120 and includes, among other components, a programmable sensing circuit 222 to sense a cardiac signal. Programmable sensing circuit 222 includes a pair of differential inputs, sense inputs 223 and 224, to sense the cardiac signal through electrodes 210A and 210B. Electrodes 210A and 210B are configured and placed in locations selected for sensing a signal approximating the surface ECG in body 102. In one embodiment, programmable sensing circuit 222 is programmable for a frequency response suitable for sensing the wireless ECG. In one embodiment, programmable sensing circuit 222 is programmable for at least a frequency response suitable for sensing the wireless ECG and another frequency response suitable for sensing an intracardiac electrogram.

Figure 2B:
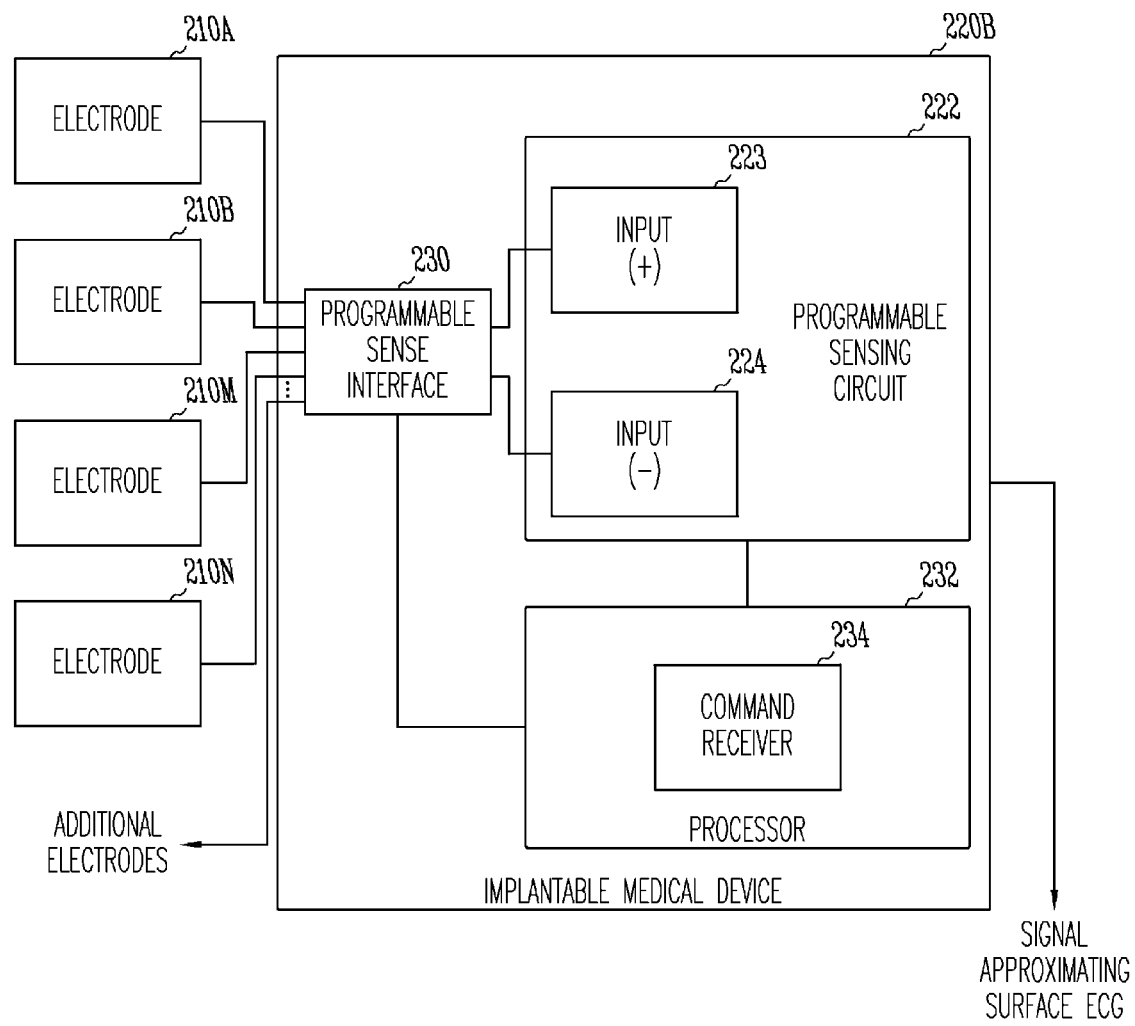
FIG. 2B is a block diagram illustrating another embodiment of portions of the circuit of the implantable medical device providing for the wireless ECG sensing.

FIG. 2B is a block diagram illustrating another embodiment of portions of the circuit of an implantable medical device 220B providing for the wireless ECG sensing. Implantable medical device 220B is another specific embodiment of implantable medical device 120 and further includes a programmable sense interface 230. Programmable sense interface 230 includes a plurality of sense interface inputs and one output connected to sense input 223 and another output connected to sense input 224. The sense interface inputs connect to a plurality of electrodes including electrodes 210A and 210B. Programmable sense interface 230 provides for selective connections between any two of the plurality of electrodes to sense inputs 223 and 224. For example, during one period of time, programmable sense interface 230 is programmed to connect electrode 210A to sense input 223 and electrode 210B to sense input 224; during another period of time, programmable sense interface 230 is programmed to connect electrode 210M to sense input 223 and electrode 210N to sense input 224. In general, electrodes 210A, 210B, 210M, and 210N each refer to any one of a plurality of electrodes available in implantable system 115 for use for the wireless ECG sensing. Programmable sense interface 230 is programmable to connect a first pair of electrodes to programmable sensing circuit 222 at one time, a second pair of electrodes to programmable sensing circuit 222 at another time, and so forth. If implantable medical device 220B includes a multi-channel sensing circuit, such as multiple units of programmable sensing circuit 222 in parallel, programmable sense interface 230 is programmable to connect multiple pairs of electrodes each to one sensing channel to allow simultaneous sensing of multiple signals each approximating one surface ECG vector.

Implantable medical device 220B further includes a processor 232 to control its operation. Processor 232 includes a command receiver 234 to receive an ECG acquisition command and produces an ECG acquisition signal to start sensing the cardiac signal. The cardiac signal, i.e., the signal approximating the surface ECG, is being sensed while the ECG acquisition signal is present in implantable medical device 220B. If the ECG acquisition signal is present, programmable sensing circuit 222 and programmable sense interface 230 are both programmed for sensing the signal approximating the surface ECG. The ECG acquisition command is generated either from external system 155 or from within implantable medical device 220B. In one embodiment, a user causes the ECG acquisition command to be transmitted to implantable medical device 220B when the surface ECG is needed. In another embodiment, processor 232 includes a detector to detect a predetermined condition and produces the ECG acquisition command when the predetermined condition is detected. In one specific embodiment, the detector includes an arrhythmia detector that detects an arrhythmic episode from an electrogram. In another specific embodiment, the detector includes an activity sensor such as an accelerometer sensing the body's gross physical movements and a respiratory sensor sensing minute ventilation. In one specific embodiment, to acquire the signal approximating the surface ECG during exercise, the detector produces the ECG acquisition command when the sensed activity level exceeds a predetermined threshold. Thus, the ECG acquisition is activated during exercise. In another embodiment, the activity level is used to stop the acquisition of the signal approximating the surface ECG when motion artifact on that signal becomes a concern. In one specific embodiment, the detector detects the predetermined condition and produces the ECG acquisition command on a continuous basis. In another specific embodiment, the detector detects the predetermined condition and produces the ECG acquisition command according to a built-in or user-programmable schedule, such as on an hourly, daily, weekly, or other periodic basis. In this embodiment, processor 232 includes a detection timer to activate and time the detection of the predetermined condition according to the built-in or user-programmable schedule.

In FIGS. 3A-F, various embodiments of electrodes 210A-B (or 210M-N) are referenced as 210AA-BA, 210AB-BB, 210AC-BC, 210AD-BD, 210AE-BE, and 210AF-BF. In one embodiment, to sense the signal approximating the surface ECG, electrode 210A is electrically connected to sense input 223, and electrode 210B is electrically connected to sense input 224, where electrodes 210A-B include one of electrode pairs 210AA-BA, 210AB-BB, 210AC-BC, 210AD-BD, 210AE-BE, and 210AF-BF. In another embodiment, to sense the signal approximating the surface ECG, programmable sense interface 230 is programmed to provide an electrical connection between electrode 210A and sense input 223 and another electrical connection between electrode 210B and sense input 224, where electrodes 210A-210B include one of electrode pairs 210AA-BA, 210AB-BB, 210AC-BC, 210AD-BD, 210AE-BE, and 210AF-BF. FIG. 3G illustrates an electrode system allowing multiple signals each approximating one surface ECG vector.

Figure 3A:
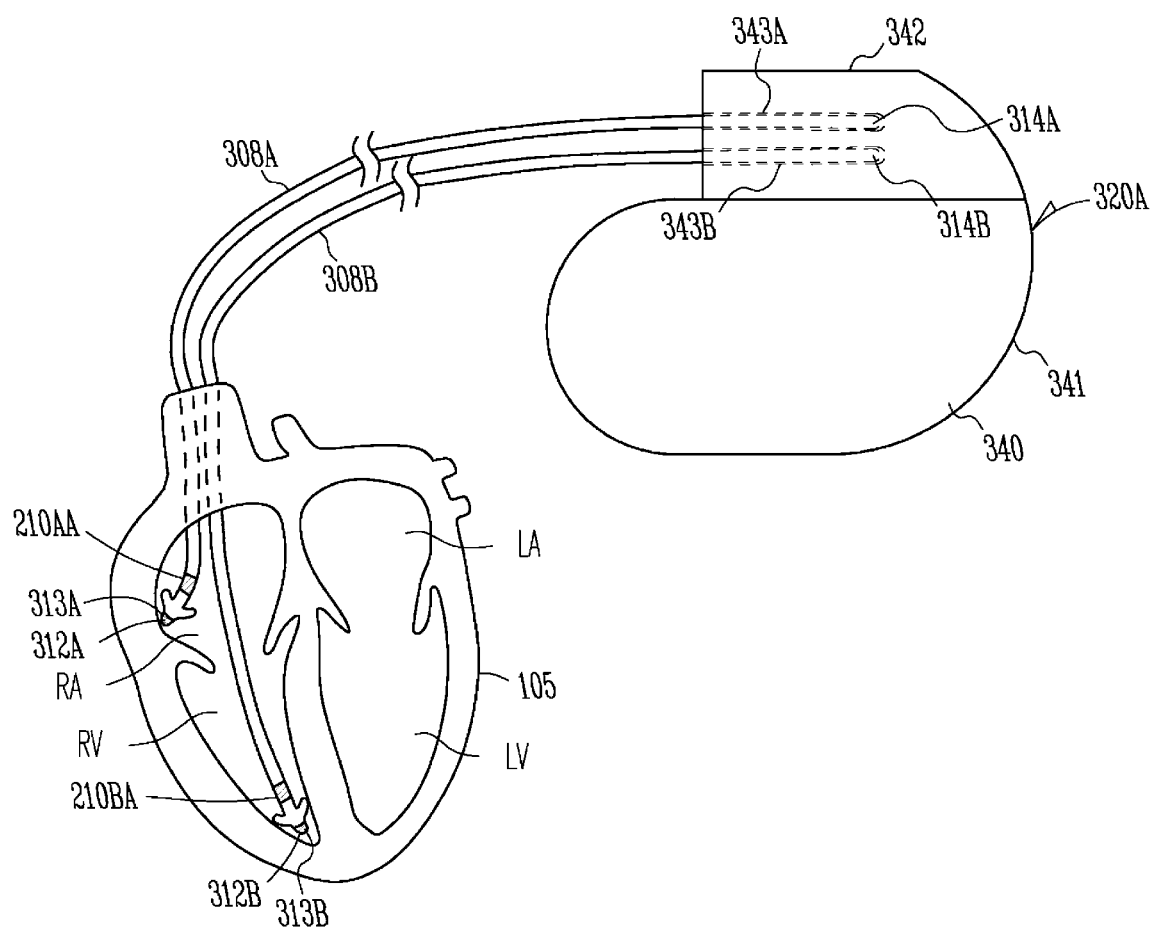
FIG. 3A is an illustration of one exemplary electrode system for the wireless ECG sensing.

FIG. 3A is an illustration of one exemplary electrode system for the wireless ECG sensing. An implantable medical device 320A, which is a specific embodiment of implantable medical device 120, is electrically connected to heart 105 through a lead system including, but not being limited to, leads 308A and 308B. Electrodes used for the wireless ECG sensing are selected from pacing electrodes of the lead system.

Implantable medical device 320A includes a hermetically sealed can 341 to house its circuit. The circuit housed in can 341 includes at least portions of programmable sensing circuit 222. Can 341 has an outer surface subject to contact with body tissue. Can 341 includes or provides for a base of a can electrode 340. At least a portion of the outer surface of can 341 is made of electrically conductive material. In one embodiment, can 341 is used as can electrode 340. In one specific embodiment, can electrode 340 includes at least one conductive portion of can 341. In another embodiment, can electrode 340 is incorporated onto the outer surface of can 341. Can electrode 340 is electrically insulated from any conductive portion of can 341 using a non-conductive layer. In one specific embodiment, a hermetically sealed feedthrough including a conductor provides for an electrical connection between can electrode 340 and the circuit housed in can 341. A header 342 is attached to can 341 and includes connectors 343A-B providing for electrical access to the circuit housed in can 341.

As illustrated in FIG. 3A, the lead system includes an atrial pacing lead 308A and a ventricular pacing lead 308B. Atrial pacing lead 308A has a proximal end 314A and a distal end 313A. Proximal end 314A connects to connector 343A. A tip electrode 312A is located in distal end 313A. A ring electrode 210AA is located near distal end 313A, at a predetermined distance from tip electrode 312A. Ventricular pacing lead 308B has a proximal end 314B and a distal end 313B. Proximal end 314B connects to connector 343B. A tip electrode 312B is located in distal end 313B. A ring electrode 210BA is located near distal end 313B, at a predetermined distance from tip electrode 312B. In one specific embodiment, as illustrated in FIG. 3A, atrial pacing lead 308A is an RA lead, and ventricular pacing lead 308B is an RV lead. In another specific embodiment, atrial pacing lead 308A is an RA lead, and ventricular pacing lead 308B is an LV lead.

In one embodiment, to sense the signal approximating the surface ECG, the ring electrode of the RA lead (electrode 210AA) is electrically connected to sense input 223, and the ring electrode of the RV (or LV) lead (electrode 210BA) is electrically connected to sense input 224. In another embodiment, to sense the signal approximating the surface ECG, programmable sense interface 230 is programmed to provide an electrical connection between the ring electrode of the RA lead (electrode 210AA) and sense input 223 and another electrical connection between the ring electrode of the RV (or LV) lead (electrode 210BA) and sense input 224.

Figure 3B:
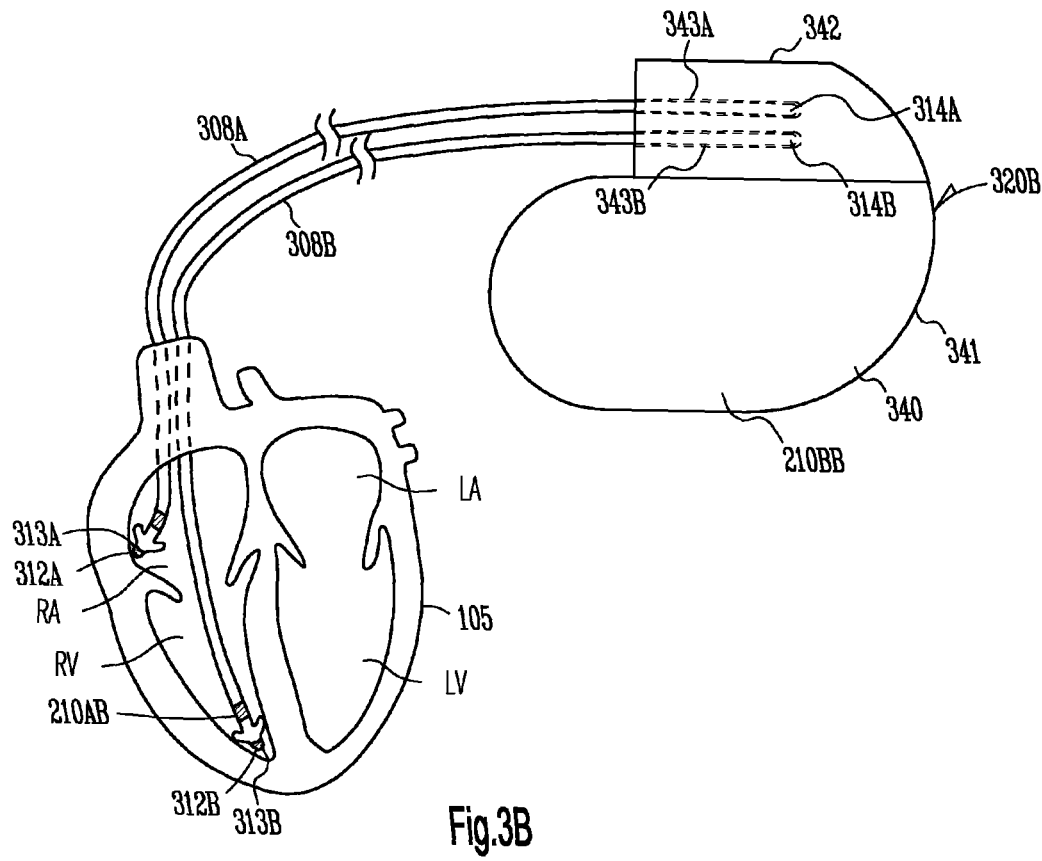
FIG. 3B is an illustration of another exemplary electrode system for the wireless ECG sensing.

FIG. 3B is an illustration of another exemplary electrode system for the wireless ECG sensing. An implantable medical device 320B, which is another specific embodiment of implantable medical device 120, is electrically connected to heart 105 through the lead system including leads 308A and 308B. The ring electrode of ventricular pacing lead 308B is used as electrode 210AB, and can electrode 340 is used as electrode 210BB, for sensing a signal approximating the surface ECG. In one specific embodiment, as illustrated in FIG. 3B, ventricular pacing lead 308B is an RV lead. In another specific embodiment, ventricular pacing lead 308B is an LV lead.

In one embodiment, to sense the signal approximating the surface ECG, the ring electrode of the RV (or LV) lead (electrode 210AA) is electrically connected to sense input 223, and can electrode 340 (electrode 210BA) is electrically connected to sense input 224. In another embodiment, to sense the signal approximating the surface ECG, programmable sense interface 230 is programmed to provide an electrical connection between the ring of the RV (or LV) lead (electrode 210AA) and sense input 223 and another electrical connection between can electrode 340 (electrode 210BA) and sense input 224.

Figure 3C:
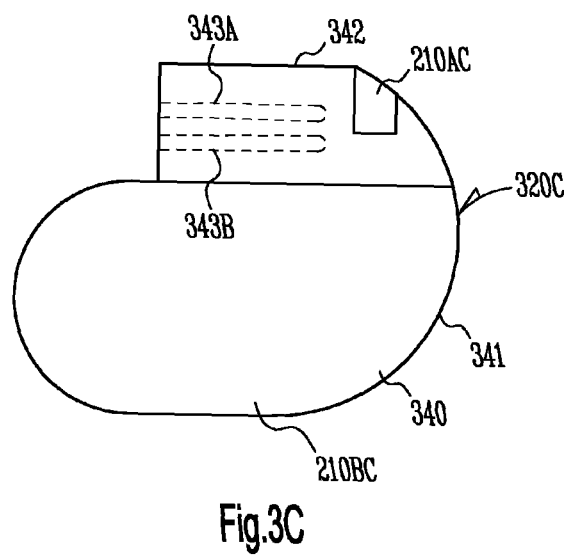
FIG. 3C is an illustration of another exemplary electrode system for the wireless ECG sensing.

FIG. 3C is an illustration of another exemplary electrode system for the wireless ECG sensing. Implantable medical device 320C is another specific embodiment of implantable medical device 120. An electrode 210AC is incorporated onto header 342. In one specific embodiment, implantable medical device 320C includes an impedance sensor functioning as a respiratory sensor sensing an impedance signal indicative of minute ventilation. Electrode 210AC is an indifferent electrode of the impedance sensor. Can electrode 340 is used as electrode 210BC.

In one embodiment, to sense the signal approximating the surface ECG, electrode 210AC (e.g., the indifferent electrode of the impedance sensor) is electrically connected to sense input 223, and electrode 210BC (can electrode 340) is electrically connected to sense input 224. In another embodiment, to sense the signal approximating the surface ECG, programmable sense interface 230 is programmed to provide an electrical connection between electrode 210AC (e.g., the indifferent electrode of the impedance sensor) and sense input 223 and another electrical connection between electrode 210BC (can electrode 340) and sense input 224.

In another embodiment, multiple electrodes are incorporated onto header 342. Any of electrodes are either dedicated for sensing the signal approximating the surface ECG or also used for other purposes. Any of such electrodes can function as electrode 210AC.

Figure 3D:
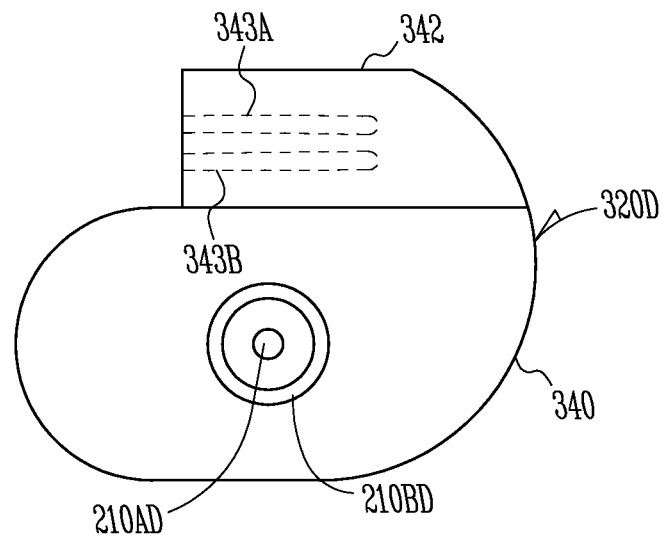
FIG. 3D is an illustration of another exemplary electrode system for the wireless ECG sensing.

FIG. 3D is an illustration of another exemplary electrode system for the wireless ECG sensing. Implantable medical device 320D is another specific embodiment of implantable medical device 120. Concentric electrodes are incorporated onto the outer surface of can 341. The concentric electrodes are insulated from the conductive portion of can 341 with a non-conductive layer. As shown in FIG. 3D, the pair of concentric electrodes include an inner electrode 210AD and an outer electrode 210BD. Inner electrode 210AD has a circular shape. Outer electrode 210BD has a ring shape. In one embodiment, inner electrode 210AD has a surface area of about 15 to 50 mm$^2$, and the outer electrode has a surface area of about 50 to 150 mm$^2$. In one specific embodiment, inner electrode 210AD has a surface area of about 31.7 mm$^2$, and the outer electrode has a surface area of about 87.1 mm$^2$. In one embodiment, a hermetically sealed feedthrough including a conductor provides for an electrical connection between inner electrode 210AD and the circuit housed in can 341, and another hermetically sealed feedthrough including a conductor provides for another electrical connection between outer electrode 210BD and the circuit housed in can 341. In another embodiment, a hermetically sealed feedthrough including two conductors provides for electrical access to the circuit housed in can 341 for both inner electrode 210AD and outer electrode 210BD.

In one embodiment, to sense the signal approximating the surface ECG, inner electrode 210AD is electrically connected to sense input 223, and outer electrode 210BD is electrically connected to sense input 224. In another embodiment, to sense the signal approximating the surface ECG, programmable sense interface 230 is programmed to provide an electrical connection between the inner electrode 210AD and sense input 223 and another electrical connection between outer electrode 210BD and sense input 224.

Figure 3E:
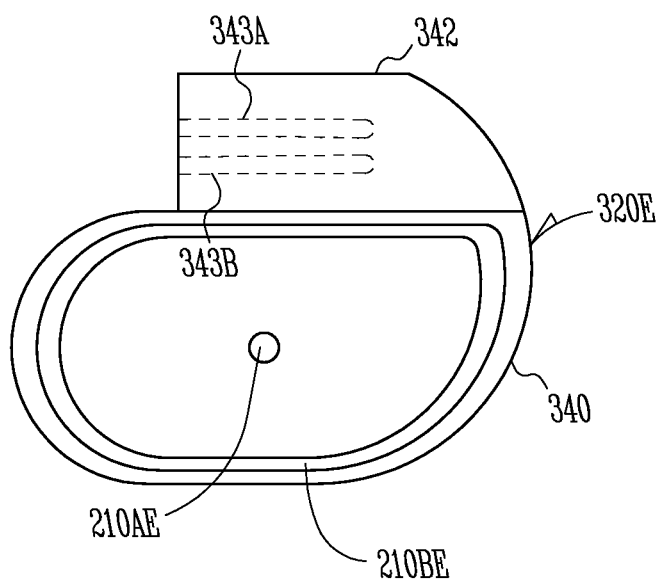
FIG. 3E is an illustration of another exemplary electrode system for the wireless ECG sensing.

FIG. 3E is an illustration of another exemplary electrode system for the wireless ECG sensing. Implantable medical device 320E is another specific embodiment of implantable medical device 120. A pair of concentric electrodes is incorporated (attached) onto the outer surface of can 341. The concentric electrodes are electrically insulated from the conductive portion of can 341 using a non-conductive layer. As shown in FIG. 3E, the pair of concentric electrodes includes an inner electrode 210AE and an outer electrode 210BE. Inner electrode 210AE has a circular shape. Outer electrode 210BE has a shape approximating the contour of can 341. In one embodiment, inner electrode 210AE has a surface area of about 3 to 12 mm$^2$, and the outer electrode has a surface area of about 100 to 250 mm$^2$. In one specific embodiment, inner electrode 210AE has a surface area of about 7.9 mm$^2$, and the outer electrode has a surface area of about 170 mm$^2$. In one embodiment, a hermetically sealed feedthrough including a conductor provides for an electrical connection between inner electrode 210AE and the circuit housed in can 341, and another hermetically sealed feedthrough including a conductor provides for another electrical connection between outer electrode 210BE and the circuit housed in can 341. In another embodiment, a hermetically sealed feedthrough including two conductors provides for electrical access to the circuit housed in can 341 for both inner electrode 210AE and outer electrode 210BE.

In one embodiment, to sense the signal approximating the surface ECG, inner electrode 210AE is electrically connected to sense input 223, and outer electrode 210BE is electrically connected to sense input 224. In another embodiment, to sense the signal approximating the surface ECG, programmable sense interface 230 is programmed to provide an electrical connection between inner electrode 210AE and sense input 223 and another electrical connection between outer electrode 210BE and sense input 224.

Figure 3F:
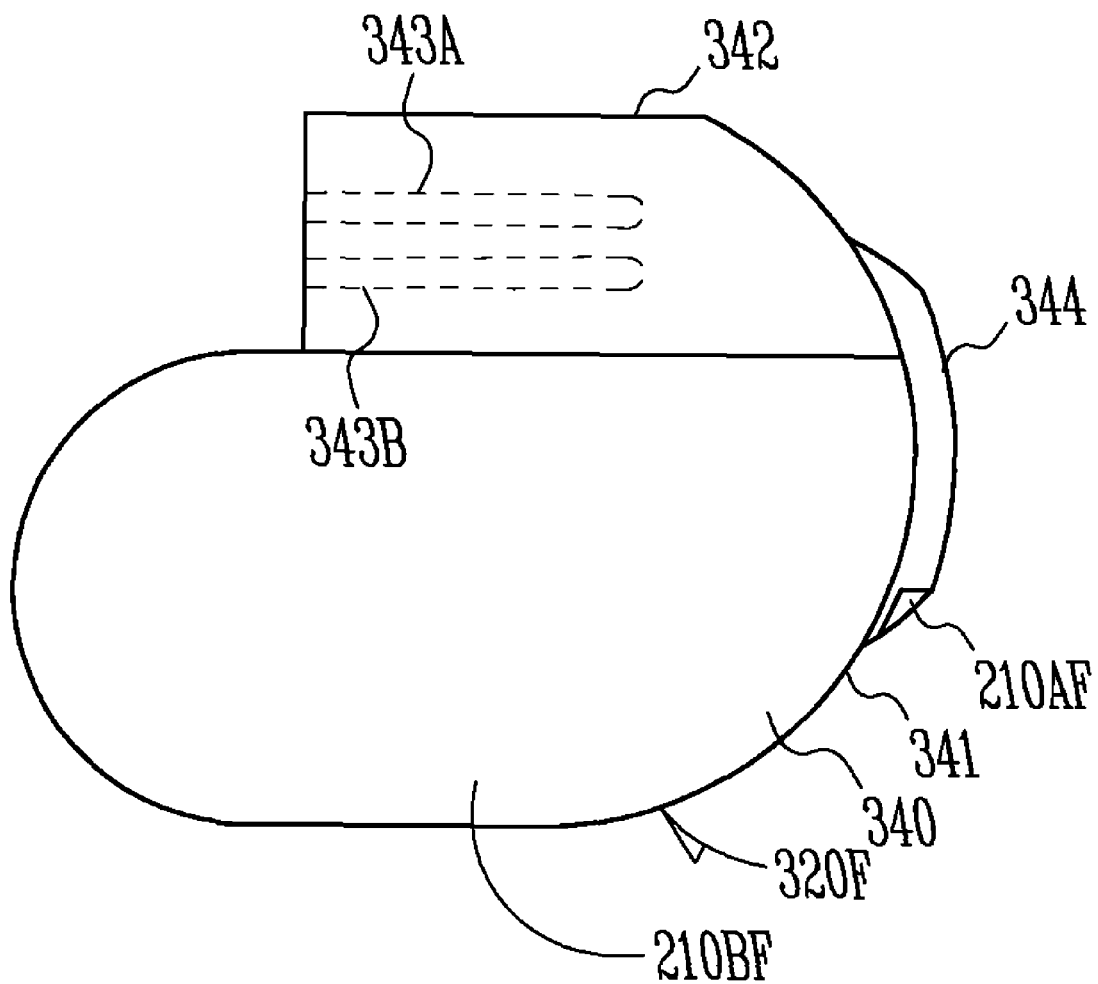
FIG. 3F is an illustration of another exemplary electrode system for the wireless ECG sensing.
Figure 3G:
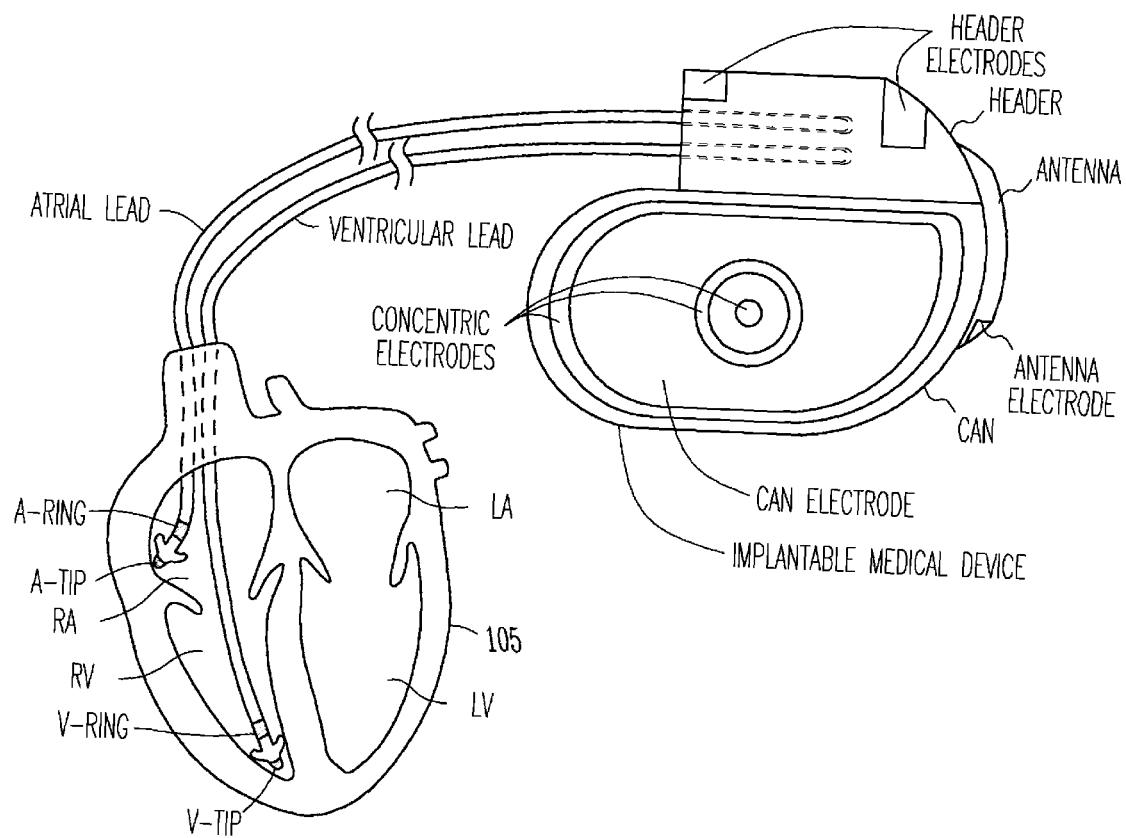
FIG. 3G is an illustration of an exemplary electrode system for multiple vector wireless ECG sensing.

FIG. 3F is an illustration of another exemplary electrode system for the wireless ECG sensing. Implantable medical device 320F is another specific embodiment of implantable medical device 120. Implantable medical device 320F includes an antenna 344 for radio-frequency telemetry. Antenna 344 is electrically connected to the circuit housed in can 341. In one embodiment, as illustrated in FIG. 3F, antenna 344 projects from header 342 and extends along one side of can 341. In one embodiment, antenna 344 includes a metal conductor with a distal portion exposed for functioning as an antenna electrode 210AF. Can electrode 340 is used as electrode 210BF.

In one embodiment, to sense the signal approximating the surface ECG, antenna 344/electrode 210AF is electrically connected to sense input 223, and can electrode 340 is electrically connected to sense input 224. In another embodiment, to sense the signal approximating the surface ECG, programmable sense interface 230 is programmed to provide an electrical connection between antenna 344/electrode 210AF and sense input 223 and another electrical connection between can electrode 340 and sense input 224.

It is to be understood that the embodiments discussed with reference to FIGS. 3A-E are intended to be examples but not limitations. Other electrode configurations and selections are usable as long as they provide for sensing of signals that approximates the surface ECG or otherwise contains valuable information for diagnostic and/or therapeutic purposes. In various embodiments in which multiple ECG vectors are needed, multiple pairs of electrodes are selected, simultaneously or one at a time, for a multi-channel wireless ECG sensing. In one specific embodiment, multiple signals are sensed to approximate a standard multi-lead surface ECG recording. In another specific embodiment, multiple signals are sensed based on needs of specific information for particular diagnostic purposes. The signals do not necessarily approximate standard surface ECG vectors.

FIG. 3G is an illustration of an exemplary electrode system allowing such multiple vector wireless ECG sensing. As illustrated in FIG. 3G, the electrode system includes all the electrodes discussed above with reference to FIGS. 3A-F. That is, the electrode system includes the tip and ring electrodes of an atrial lead (A-TIP and A-RING), the tip and ring electrodes of one or more ventricular leads (V-TIP and V-RING), the can of the implantable medical device (can electrode), one or more electrodes incorporated onto the header of the implantable medical device (header electrodes), two or more concentric electrodes, and the antenna electrode. In one embodiment, to sense the signal approximating the surface ECG, programmable sense interface 230 is programmable to provide an electrical connection between one of these electrodes and sense input 223 and another electrical connection between another one of these electrodes and sense input 224. In other words, programmable sense interface 230 is programmable to provide electrode connection between programmable sensing circuit 222 and one pair of electrode selected from any two electrodes available in implantable system 115. In one embodiment, programmable sense interface 230 is programmed to connect several pairs of electrodes to programmable sensing circuit 222, one at a time, to obtain multiple signals (vectors). In another embodiment, programmable sense interface 230 is programmed to connect several pairs of electrodes each to one channel of a multi-channel sensing circuit (such as multiple units of programmable sensing circuit 222 in parallel), to obtain multiple signals (vectors) simultaneously. In these embodiments, the pair or pairs of electrodes each include any combination of the electrodes for sensing the signal approximating the surface ECG, including electrodes 210AA-AF, electrodes 210BA-BF, and any other electrodes in implantable system 115. In one specific embodiment, the implantable medical device includes the two (first and second) header electrodes and the can electrode for the wireless ECG sensing. ECG vectors are sensed between (1) the first and second header electrodes, (2) the first header electrode and the can electrode, and (3) the second header electrode and the can electrode. In another specific embodiment, the implantable medical device includes one of the header electrodes, the antenna electrode, and the can electrode for the wireless ECG sensing. ECG vectors are sensed between (1) the header electrode and the antenna electrode, (2) the header electrode and the can electrode, and (3) the antenna electrode and the can electrode. In another specific embodiment, the implantable medical device includes the two (first and second) header electrodes, the antenna electrode, and the can electrode for the wireless ECG sensing. ECG vectors are sensed between (1) the first and second header electrodes, (2) the first header electrode and the antenna electrode, (3) the first header electrode and the can electrode, (4) the second header electrode and the antenna electrode, (5) the second header electrode and the can electrode, and (6) the antenna electrode and the can electrode. Other specific embodiments involving any electrode combinations for the wireless ECG sensing will be employed based on possible diagnostic and other medical needs and considerations.

Figure 4:
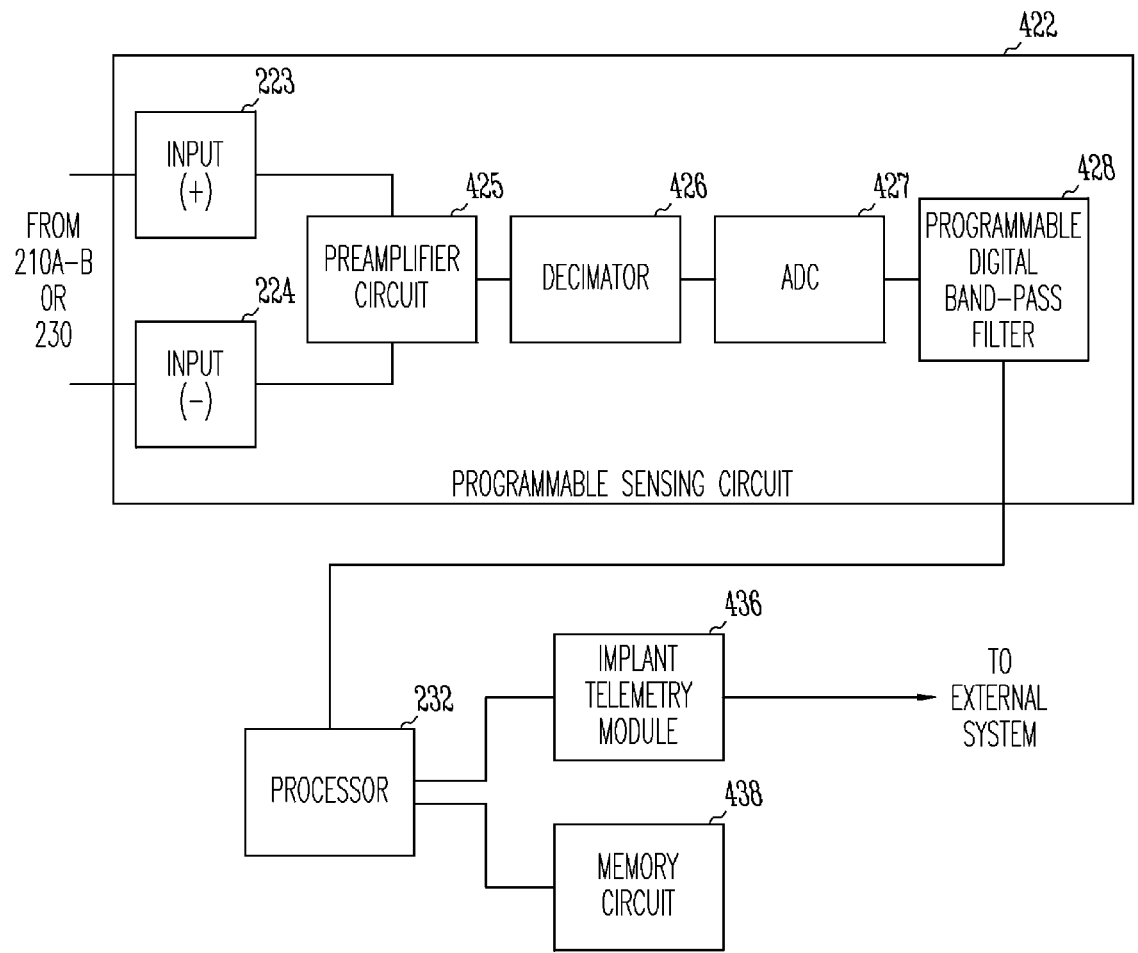
FIG. 4 is a block diagram showing one embodiment of portions of the circuit of the implantable medical device.

FIG. 4 is a block diagram showing one embodiment of portions of the circuit of implantable medical device 120, including a programmable sense circuit 422, processor 232, an implant telemetry module 436, and a memory circuit 438.

Programmable sensing circuit 422, which is a specific embodiment of programmable sensing circuit 222 includes inputs 223 and 224, a preamplifier circuit 425, a decimator 426, an analog-to-digital converter (ADC) 427, and a digital band-pass filter 428. In one embodiment, preamplifier circuit 425 includes an analog amplifier and an analog filter. In another embodiment, programmable sense interface 230 includes the analog filter. Programmable sensing circuit 422 has a gain and a frequency response determined by the characteristics of preamplifier circuit 425 and digital band-pass filter 428. In one embodiment, the gain and the frequency response of programmable sensing circuit 422 are each programmable. The gain includes a gain programmable for at least a gain selectable for being suitable for sensing a signal approximating the surface ECG and a gain selectable for being suitable for sensing intracardiac electrogram. The frequency response includes a pass band programmable for at least a surface ECG pass band selectable for being suitable for sensing a signal approximating the surface ECG and an intracardiac electrogram pass band selectable for being suitable for sensing intracardiac electrogram. Each pass band is defined by a low cutoff frequency and a high cutoff frequency. At least one of the low cutoff frequency and the high cutoff frequency is programmable. The low cutoff frequency and/or the high cutoff frequency are programmed by programming one or both of preamplifier circuit 425 and digital band-pass filter 428. The surface ECG pass band includes a low cutoff frequency chosen to ensure that the interested low-frequency components are included in the sensed signal approximating the surface ECG. In one embodiment, the low cutoff frequency of the surface ECG pass band is programmable for 4 Hz or less. In another embodiment, the low cutoff frequency of the surface ECG pass band is programmable to 0.5 Hz or less. In one embodiment, the low cutoff frequency for programmable sensing circuit 422 is programmable in a range of 0.1 Hz to 30 Hz, and the high cut-off frequency for programmable sensing circuit 422 is programmable in a range of 30 Hz to 150 Hz. When the pass band is programmed to the surface ECG pass band, the low cutoff frequency is programmed to a value between 0.1 Hz to 4 Hz, and the high cut-off frequency is programmed to a value between 30 Hz to 100 Hz. When the pass band is programmed to the intracardiac electrogram pass band, the low cutoff frequency is programmed to a value between 10 Hz to 30 Hz, and the high cut-off frequency is programmed to a value between 60 Hz to 150 Hz.

Implant telemetry module 436 transmits the sensed signal approximating the surface ECG to external system 155 via telemetry link 145. In one embodiment, command receiver 234 receives the ECG acquisition command from external system 155 through implant telemetry module 436.

Memory circuit 438 includes an ECG storage to store the sensed signal approximating the surface ECG. In one embodiment, upon receiving the ECG acquisition command, implantable medical device 120 senses the signal approximating the surface ECG and transmits the sensed signal to external system 155 in substantially real time. In another embodiment, upon receiving the ECG acquisition command, implantable medical device 120 senses the signal approximating the surface ECG and stores the sensed signal in the ECG storage to be transmitted at a later time.

Figure 5:
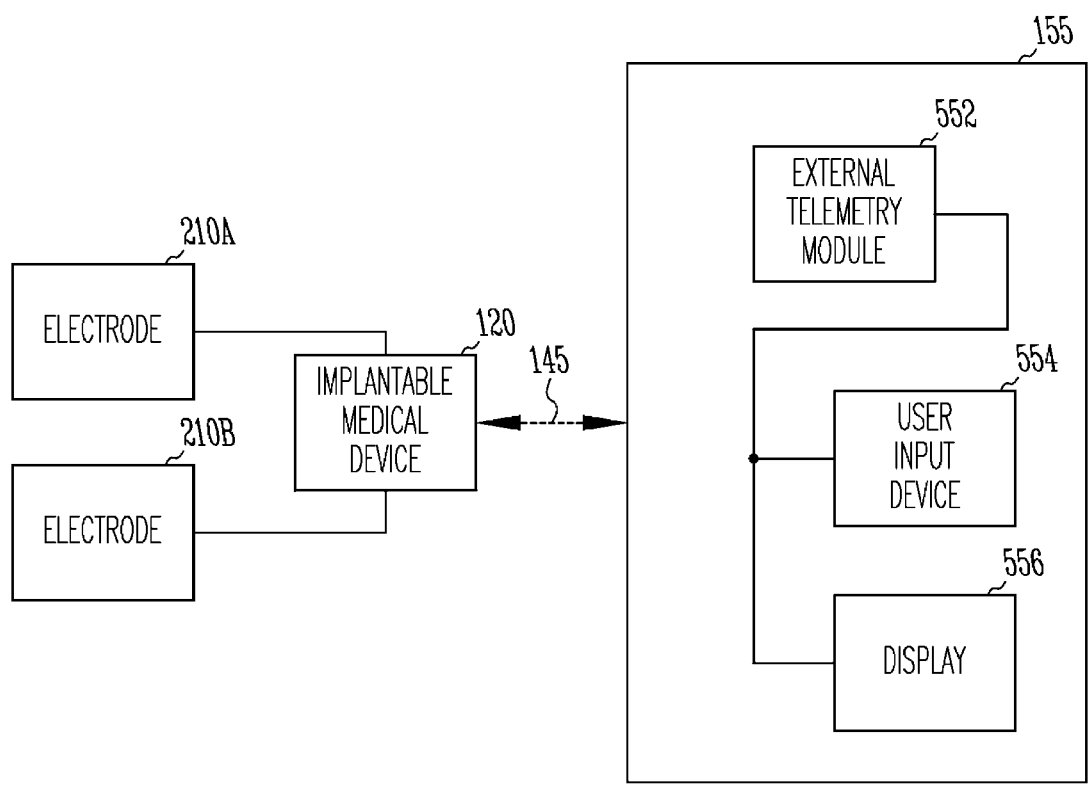
FIG. 5 is a block diagram showing one embodiment of portions of the CRM system including the implantable medical device and the external system.

FIG. 5 is a block diagram showing portions of CRM system 100 including electrodes 210A and 210B, implantable medical device 120, and external system 155. External system 155 includes, among other components, an external telemetry module 552, a user input device 554, and a display 556. External telemetry module 552 receives the signal approximating the surface ECG via telemetry link 145 from implantable medical device 120, and transmits the ECG acquisition command to implantable medical device 120. User input device 554 receives the ECG acquisition command entered by the user. Display 556 visually presents the signal approximating the surface ECG. In one embodiment, the signal approximating the surface ECG is presented in substantially real time as it is being sensed by implantable medical device 120. In another embodiment, the signal approximating the surface ECG is displayed as it is extracted from the ECG storage of memory circuit 438 in implantable medical device 120.

In one embodiment, external system 155 includes a programmer. In another embodiment, external system 155 is a patient management system including external device 150, network 160, and remote device 170, as illustrated in FIG. 1. In one specific embodiment, remote device 170 includes user input 554 and display 556. This allows the user to view either real time or stored ECG of a patient from a remote facility.

Figure 6:
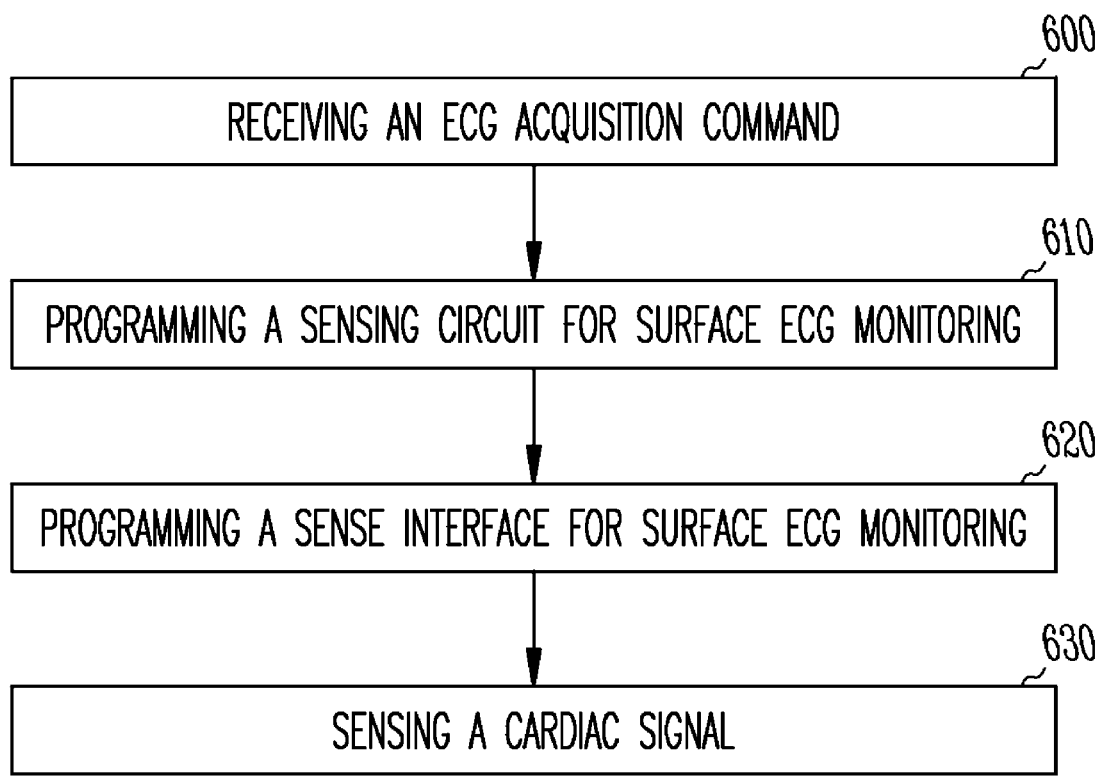
FIG. 6 is a flow chart illustrating one embodiment of a method for a wireless ECG sensing using an implantable medical device.

FIG. 6 is a flow chart illustrating one embodiment of a method for a wireless ECG sensing using a system such as CRM system 100 discussed above. The method allows sensing of a signal substituting for a surface ECG using an implantable medical device, eliminating the need for skin contact electrodes and wires/cables connecting the electrodes and an ECG recording device.

An ECG acquisition command is received by the implantable medical device at 600. In one embodiment, the ECG acquisition command is received from an external device via telemetry. In another embodiment, one or more predetermined cardiac conditions are detected by the implantable medical device, and the ECG acquisition command is generated within the implantable medical device in response to a detection of the one or more predetermined cardiac conditions.

In response to the ECG acquisition command, a sensing circuit of the implantable medical device is programmed for surface ECG monitoring at 610. This includes programming a band-pass filtering circuit with cutoff frequencies suitable for the surface ECG monitoring. In one embodiment, the low cutoff frequency is programmed to a value between about 0.1 Hz and 10 Hz, and the high cutoff frequency is programmed to a value between about 30 Hz and 100 Hz. In one specific embodiment, where maximum amount of information is desired, the low cutoff frequency is programmed to approximately 0.1 Hz, and the high cutoff frequency is programmed to approximately 100 Hz. In another specific embodiment, where the noise level is to be minimized, the low cutoff frequency is programmed to approximately 0.5 Hz, and the high cutoff frequency is programmed to approximately 50 Hz or less.

In response to the ECG acquisition command, a sense interface of the implantable medical device is programmed to electrically connect a pair of electrodes to the sensing circuit at 620. The pair of electrodes is suitable for sensing a cardiac signal approximating the surface ECG. In one embodiment, the sense interface is programmed for an electrical connection between the sensing circuit and a ring electrode of an RA pacing lead and another electrical connection between the sensing circuit and a ring electrode of an RV pacing lead. In another embodiment, the sense interface is programmed for an electrical connection between the sensing circuit and the ring electrode of the RV pacing lead and another electrical connection between the sensing circuit and a housing of the implantable medical device. In another embodiment, the sense interface is programmed for an electrical connection between the sensing circuit and an indifferent electrode of an impedance sensor included in the implantable medical device and another electrical connection between the sensing circuit and the housing of the implantable medical device. In another embodiment, the sense interface is programmed for connections between the sensing circuit and a pair of concentric electrodes incorporated onto the housing of the implantable medical device. In one specific embodiment, the concentric electrodes include an inner electrode and an outer electrode, and the sense interface is programmed for an electrical connection between the sensing circuit and the inner electrode and another electrical connection between the sensing circuit and the outer electrode.

After the sensing circuit and the sense interface are programmed, the cardiac signal approximating the surface ECG is sensed at 630. In one embodiment, the sensed cardiac signal is transmitted to the external device for a substantially real time display. In another embodiment, the sensed cardiac signal is stored in the implantable medical device and transmitted to the external device for display at a later time.

In one embodiment, the sensed cardiac signal approximating the surface ECG is displayed for measurements related to fiducial points including, but are not limited to, P wave, QRS onset, R wave, QRS offset, and T wave. In one embodiment, the sensed cardiac signal approximating the surface ECG is simultaneously displayed with the signals acquired by the implantable medical device and/or derived from these acquired signals, such as sense markers indicative of intrinsic cardiac depolarizations, pace markers indicative of pacing pulse deliveries, a minute ventilation signal, heart sounds, and markers indicative of respiratory and other mechanical events. In one embodiment, sensing the cardiac signal approximating the surface ECG enhances an overall sensing scheme for pacing and/or defibrillation therapies. In one specific embodiment, the cardiac signal approximating the surface ECG provides an independent verification of events detected from an electrogram. In another specific embodiment, the cardiac signal approximating the surface ECG provides a substitute for an electrogram in the event that the sensing system for that electrogram dysfunctions. In one embodiment, where a patient management system is used, the cardiac signal approximating the surface ECG is displayed in real time for circadian events such as nocturnal atrial fibrillation or apnea. In one specific embodiment, these events are stored for trending purposes. The trending is used to determine and display shifts in signal morphology over time.

It is to be understood that the above detailed description is intended to be illustrative, and not restrictive. For example, the wireless ECG sensing system discussed above can be implemented in any implantable medical device that includes a sensing circuit and electrodes suitable for sensing a signal approximating the surface ECG. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device configured to be coupled to a plurality of electrodes including first electrodes suitable for sensing a first type cardiac signal and second electrodes suitable for sensing a second type cardiac signal, the implantable medical device comprising:
   a command receiver configured to receive an acquisition command;
   a sensing circuit configured to be programmed in response to the acquisition command to sense the first type cardiac signal, the sensing circuit including a frequency response programmable for at least a first pass band selectable for sensing the first type cardiac signal and a second pass band selectable for sensing the second type cardiac signal; and
   a sense interface configured to be programmed in response to the acquisition command to provide first electrical connections for sensing the first type cardiac signal, the first electrical connections connecting the sensing circuit to the first electrodes.

2. The implantable medical device of claim 1, further comprising a detector configured to detect a predetermined condition and produces the acquisition command in response to a detection of the predetermined condition.

3. The implantable medical device of claim 2, further comprising a detection timer coupled to the detector, the detection timer configured to activate and time the detection of the predetermined condition based on a built-in or programmable schedule.

4. The implantable medical device of claim 1, further comprising a telemetry module coupled to the command receiver, and wherein the command receiver is configured to receive the acquisition command through the telemetry module.

5. The implantable medical device of claim 4, wherein the telemetry module is configured to transmit the sensed first type cardiac signal out of the implantable medical device.

6. The implantable medical device of claim 1, wherein the sensing circuit has a low cutoff frequency and a high cutoff frequency, wherein at least one of the low cutoff frequency and the high cutoff frequency is programmable.

7. The implantable medical device of claim 6, wherein the low cutoff frequency is programmable in a range of about 0.1 Hz to 30 Hz.

8. The implantable medical device of claim 6, wherein the high cutoff frequency is programmable in a range of about 30 Hz to 150 Hz.

9. A cardiac rhythm management system, comprising:
a plurality of electrodes including first electrodes suitable for sensing a first type cardiac signal and second electrodes suitable for sensing a second type cardiac signal; and
an implantable medical device comprising:
  a command receiver configured to receive an acquisition command;
  a sensing circuit configured to be programmed in response to the acquisition command to sense the first type cardiac signal, the sensing circuit including a frequency response programmable for at least a first pass band selectable for sensing the first type cardiac signal and a second pass band selectable for sensing the second type cardiac signal; and
  a sense interface configured to be programmed in response to the acquisition command to provide first electrical connections for sensing the first type cardiac signal, the first electrical connections connecting the sensing circuit to the first electrodes.

10. The system of claim 9, wherein the implantable medical device further comprises a detector configured to detect a predetermined condition and produces the acquisition command in response to a detection of the predetermined condition.

11. The system of claim 10, wherein the implantable medical device further comprises a detection timer coupled to the detector, the detection timer configured to activate and time the detection of the predetermined condition based on a built-in or programmable schedule.

12. The system of claim 9, wherein the implantable medical device further comprises a telemetry module coupled to the command receiver, and wherein the command receiver is configured to receive the acquisition command through the telemetry module.

13. The system of claim 9, wherein the first electrodes comprise at least one electrode incorporated onto the implantable medical device.

14. The system of claim 13, wherein the first electrodes comprise at least two electrodes incorporated onto the implantable medical device.

15. The system of claim 13, wherein the implantable medical device comprises:
  a can housing a circuit including the command receiver, the sensing circuit, and the sense interface; and
  a header attached to the can, the header including connectors providing for electrical access to the circuit,
  and wherein the at least one electrode incorporated onto the implantable medical device is incorporated onto the can.

16. The system of claim 15, wherein the first electrodes comprise a further electrode incorporated onto the can.

17. The system of claim 15, wherein the first electrodes comprise a further electrode incorporated onto the header.

18. The system of claim 15, wherein the first electrodes comprise at least two concentric electrodes incorporated onto the can, the at least two concentric electrodes including an inner electrode and an outer electrode.

19. The system of claim 18, wherein the inner electrode comprises a circular shaped electrode, and the outer electrode comprises a ring shaped electrode.

20. The system of claim 18, wherein the inner electrode comprises a circular shaped electrode, and the outer electrode comprises an electrode approximating a contour of the can.

* * * * *